US006523412B1

(12) United States Patent
McClelland et al.

(10) Patent No.: US 6,523,412 B1
(45) Date of Patent: Feb. 25, 2003

(54) APPARATUS AND METHOD FOR INSPECTING SPRING HOLD DOWN BOLTS OF AN UPPER TIE PLATE

(75) Inventors: Richard G. McClelland, Richland, WA (US); Michael D. Bowen, Kennewick, WA (US)

(73) Assignee: Framatome ANP Inc., Lynchburg, VA (US)

( * ) Notice: Subject to any disclaimer, the term of this patent is extended or adjusted under 35 U.S.C. 154(b) by 0 days.

(21) Appl. No.: 09/604,870

(22) Filed: Jun. 28, 2000

(51) Int. Cl.[7] .............................. G01N 9/24; G21C 17/00
(52) U.S. Cl. .............................. 73/634; 73/620; 73/633; 73/644; 376/245
(58) Field of Search ........................ 73/584, 661, 634, 73/627, 628, 629, 619, 620, 644, 622, 633; 376/245

(56) References Cited

U.S. PATENT DOCUMENTS

| | | | |
|---|---|---|---|
| 4,522,064 A | * 6/1985 | McMillan | 73/592 |
| 4,818,470 A | * 4/1989 | Richardson et al. | 376/245 |
| 4,847,037 A | * 7/1989 | Scharpenberg et al. | 376/245 |
| 5,095,753 A | * 3/1992 | Russ et al. | 73/598 |
| 5,156,050 A | * 10/1992 | Schmid et al. | 73/644 |
| 5,201,226 A | * 4/1993 | John, Jr. et al. | 73/622 |
| 5,457,997 A | * 10/1995 | Naruo et al. | 73/643 |
| 5,710,378 A | * 1/1998 | Dykes et al. | 73/601 |
| 6,137,853 A | * 10/2000 | Duckering et al. | 376/252 |

* cited by examiner

*Primary Examiner*—Hezron Williams
*Assistant Examiner*—Jacques Saint-Surin
(74) *Attorney, Agent, or Firm*—Kenyon & Kenyon

(57) ABSTRACT

The invention is directed to an apparatus and method for inspecting spring hold down bolts of an upper tie plate of a fuel rod assembly in a nuclear reactor and includes an inspection fixture adapted to be aligned with the upper tie plate of the nuclear reactor fuel rod assembly for placement into a position for rapid and easy insitu inspection of the hold down bolts of the upper tie plate. The fixture is provided with a plurality of ultrasonic transducers which are positioned on the fixture so that when the fixture is placed into the inspection position each transducer will be located proximate to one of the hold down bolts for conducting effective ultrasonic scanning of the bolt while the bolt is in place. A multi-channel ultrasonic flaw detector is connected to each of the transducers for indicating whether there are any flaws in each of the hold down bolts when the fixture is placed into the inspection position and the ultrasonic transducers are activated. A further feature of the invention is the use of spherically focused transducers for focusing the sound field at the predetermined distance from the head of the bolt in order to facilitate proper scanning of the bolt shank and thread relief, thereby greatly increasing inspection sensitivity.

22 Claims, 5 Drawing Sheets

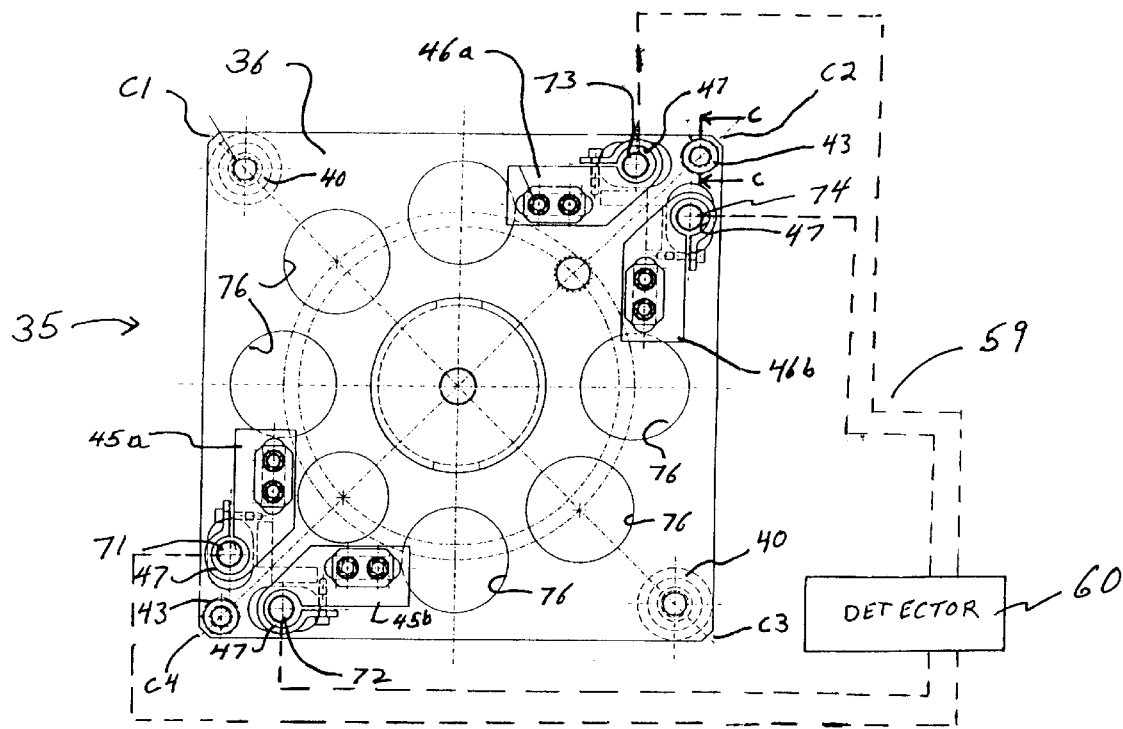
Figure 3B
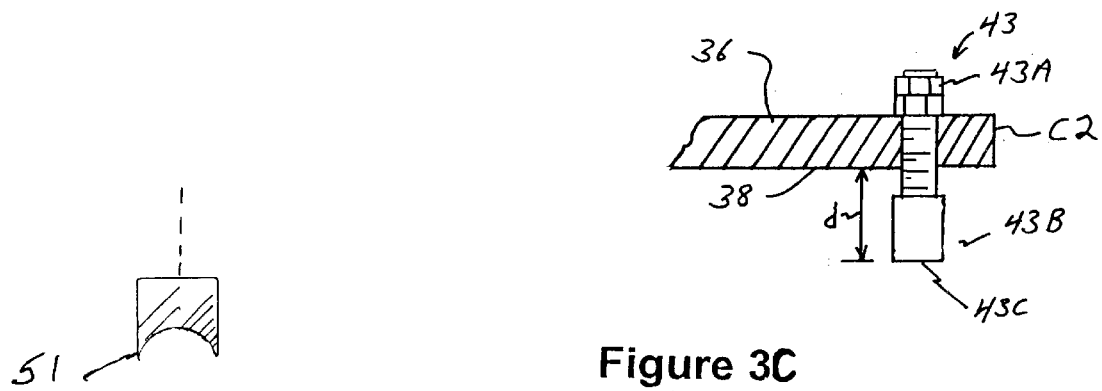
Figure 3C
Figure 4

APPARATUS AND METHOD FOR INSPECTING SPRING HOLD DOWN BOLTS OF AN UPPER TIE PLATE

FIELD OF THE INVENTION

The present invention relates generally to the field of nuclear reactors and more particularly to an apparatus and method for inspecting spring hold down bolts of an upper tie plate of a fuel rod assembly within a nuclear reactor.

BACKGROUND OF THE INVENTION

Bolt failures in nuclear reactors are frequently a consequence of irradiation. Inspection of bolts in the core area and in the spent fuel pool is therefore important.

Nuclear reactors of well known design typically utilize assemblies of fuel rods which are arranged with their axes parallel to each other in a generally square or rectangular matrix. Appropriate spacers are employed to arrange the fuel rods in the desired matrix. An element known as a tie plate is commonly used at least at one end of the fuel rod assembly in order to facilitate movement of the assembly and to constrain the rods. The fuel rod assemblies are supported within the reactor in a generally vertical orientation and the tie plate located at the upper end of the vertical arrangement, known as the upper tie plate, is used for proper positioning of the fuel rods in the desired matrix. Common designs for the upper tie plate incorporate leaf springs, usually positioned along the horizontal edges of the tie plate, in order to provide proper tensioning of the tie plate against other elements in the reactor. Corner clamps are used at opposing corners of the tie plate to hold down at least one end of the leaf springs. The corner clamps are angle assemblies secured to the tie plate by a pair of hold down bolts. Other corners of the tie plate are usually provided with guide pin holes for receiving guide pins to properly align the tie plate with other assembly elements in the reactor.

It has been found that the leaf spring hold down bolts sometime develop flaws, such as fine cracks, when subjected to reactor cycling. When such flaws develop, the hold down bolts may fail to adequately hold the leaf springs in proper position. The springs that are used to provide tensioning forces therefore no longer function properly. This can result in certain parts, such as springs, clamps, and/or bolts, of the upper tie plate becoming loose. If the bolts break, the leaf springs fail to function properly and the fuel rod assembly can move vertically, which is not desirable. In addition, appropriate fuel assembly handling equipment might not be able to properly grip the assembly for desired movement or placement. When the bolts fail, the corner clamps that position and secure the springs become free. This allow the springs to move freely (still constrained by the upper tie plate). When the fuel assembly is to be moved, the fuel handling grapple must interface with the upper tie plate alignment hole and have clearance to engage with the inside of the upper tie plate lip. In an assembly with broken bolts, the springs typically block access to the inside lip of the upper tie plate, making engagement and grappling impractical. Under extreme cases, the clamp block may become free and potentially damage reactor internals. Fuel assemblies with broken bolts cannot be returned to the core until repaired.

Even without knowing whether certain bolts indeed have flaws that could lead to serious defects, replacement of the upper tie plates is nonetheless undertaken at great cost and involve time consuming procedures. No effective means for directly inspecting the bolts to determine the pressure of incipient flaws without having to remove them is currently in use.

OBJECTS OF THE INVENTION

It is accordingly a general object of the present invention to provide a method and apparatus for effective and rapid inspection of the spring hold down bolts on the upper tie plate of the fuel rod assembly in order to overcome the possible needless, but expensive and time consuming, replacement of all upper tie plate assemblies when such replacement might not be necessary.

It is a more specific object of the present invention to provide an apparatus and method for quick, easy and inexpensive inspection of the hold down bolts of the corner clamps for the upper tie plate while the bolts remain in place.

It is a still further specific object of the present invention to provide an apparatus for conducting such inspection which includes a fixture that is adapted to be aligned with the upper tie plate and placed into an inspection position which is located proximate to the tie plate for conducting effective inspection of the hold down bolts insitu.

Yet a further object of the present invention is to provide a means to avoid costly and unnecessary replacement of the upper tie plates which have certain bolts with no flaws without disassembling the hold down assembly arrangement, thus saving significant time and money when such disassembly is not necessary.

A further more specific object of the present invention is to provide a method and apparatus for conducting such inspection utilizing ultrasonic transducers carried by probes on a fixture which can be placed in proximity to the upper tie plate so that ultrasonic scanning of each bolt can be rapidly and inexpensively conducted to determine whether or not any of the bolts have early indications of flaws.

Yet another object of the present invention is to utilize spherically focused ultrasonic transducers which are provided with lenses that cause the focus of the sound field of the transducer at a prescribed distance, which can be located at a position at the bottom of the bolt head so that the sound field beyond the focal point is capable of encompassing the bolt shank above the bolt thread relief. Providing transducers of this type and containing the sound field in this area of the bolt greatly increases test sensitivity.

Another object of the present invention is to provide an apparatus and method for inspecting hold down bolts by placing a fixture on the tie plate assembly and simply viewing ultrasonic data from scanning each bolt.

A further object of the present invention is to provide a rapid and effective means for detecting flaws, such as cracks, having a depth as small as one tenth of one inch.

Other objects, features and advantages of the present invention will become apparent from the detailed description hereinafter.

BRIEF DESCRIPTION

The invention is directed to an apparatus and method for inspecting spring hold down bolts of an upper tie plate of a fuel rod assembly in a nuclear reactor and includes an inspection fixture adapted to be aligned with the upper tie plate of the nuclear reactor fuel rod assembly for placement into a position for rapid and easy insitu inspection of the hold down bolts of the upper tie plate. The fixture is provided with a plurality of ultrasonic transducers which are located on the fixture so that when the fixture is placed into the inspection position each transducer will be positioned proximate to one of the hold down bolts for conducting effective ultrasonic scanning of the bolt while the bolt is in place. A multi-channel ultrasonic flaw detector is connected to each of the transducers for indicating whether there are any flaws in each of the hold down bolts when the fixture is placed into the inspection position and the ultrasonic transducers are activated. A further feature of the invention is the use of spherically focused transducers for focusing the sound field at a predetermined distance from the head of the bolt in order to facilitate proper scanning of the bolt shank and thread relief, thereby greatly increasing inspection sensitivity.

The foregoing and other features of the present invention are more fully described with reference to the following drawings annexed hereto.

BRIEF DESCRIPTION OF THE DRAWINGS

FIG. 3B is a bottom plan view of the inspection fixture shown in FIG. 3A;

FIG. 3C is a sectional view along lines C—C of FIG. 3B;

FIG. 4 is a schematic sectional view of a spherical transducer head utilized in the present invention;

DESCRIPTION OF THE INVENTION

Figure 1:
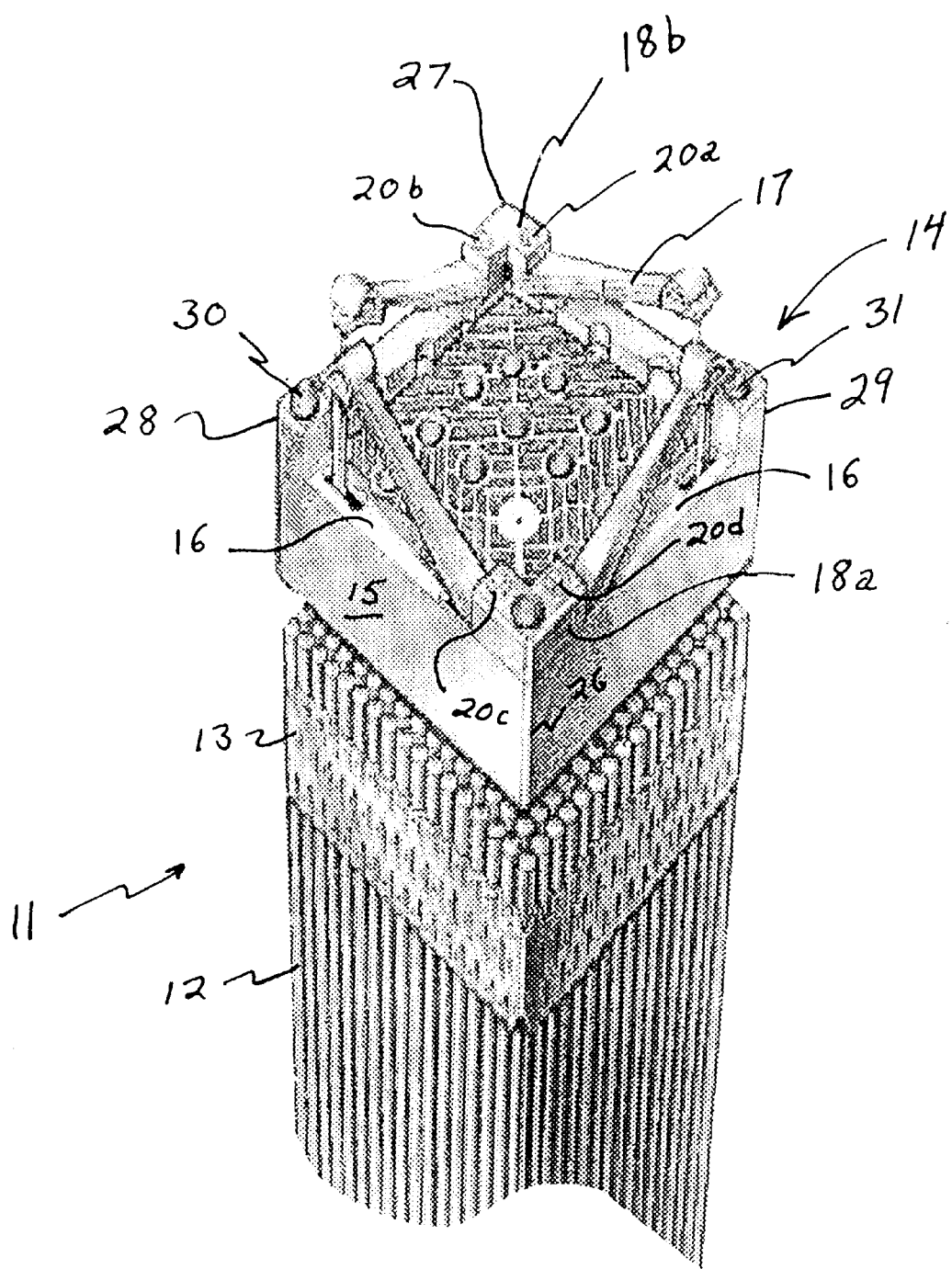
FIG. 1 is a perspective view of a vertically arranged fuel rod assembly illustrating the upper tie plate and hold down bolt assemblies.
Figure 2:
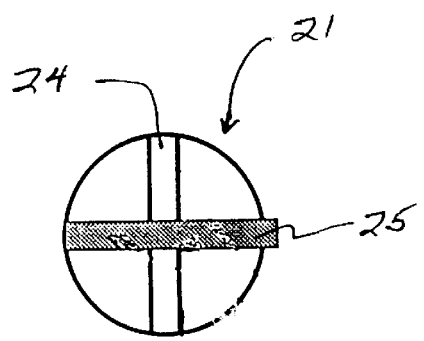
FIG. 2 is a top plan view of a single hold down bolt.
Figure 3A:
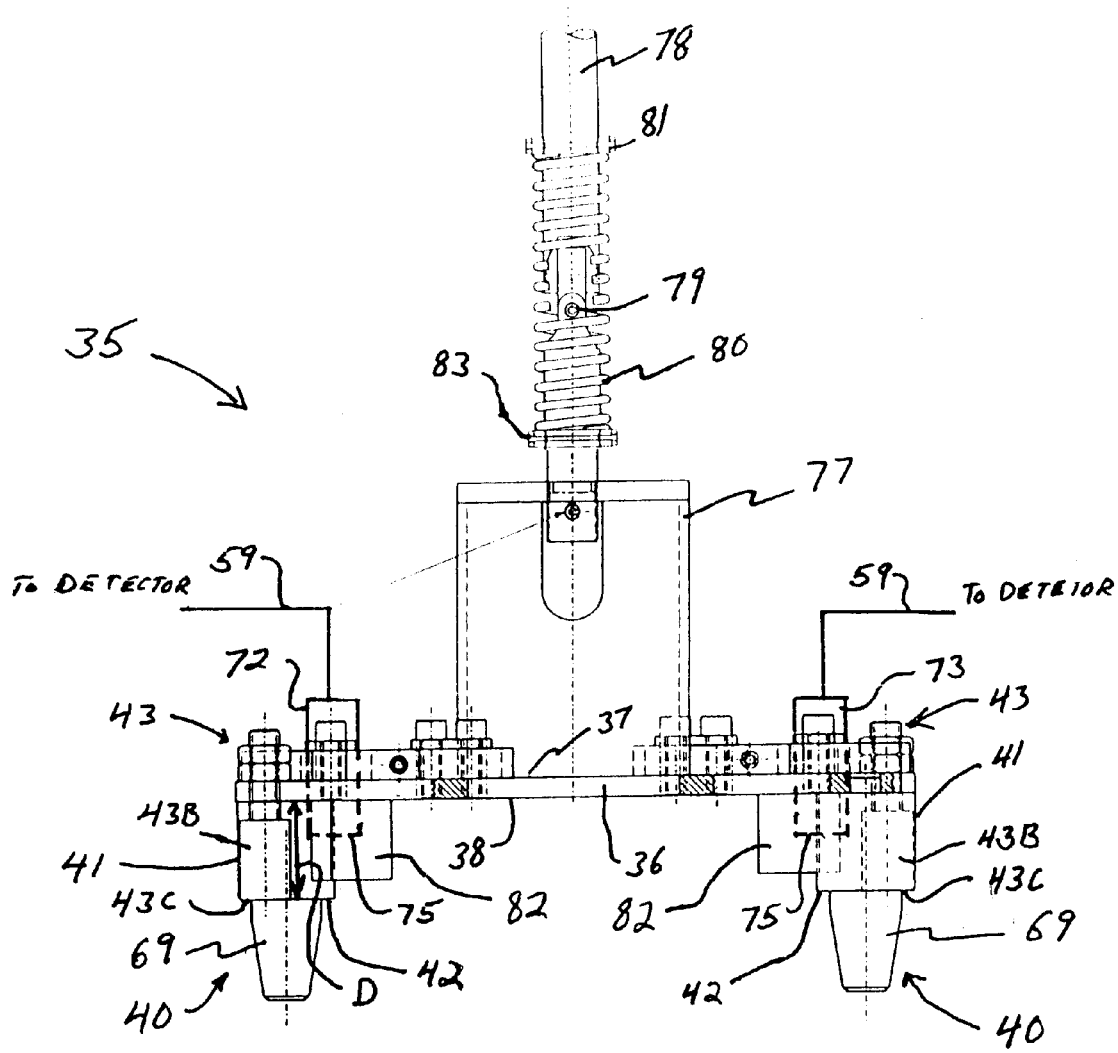
FIG. 3A is a side elevational view of the inspection fixture of the present invention.

Referring now to the drawings, and with particular reference to FIG. 1, reference numeral 11 denotes a typical arrangement of fuel rods 12. The arrangement 11 of fuel rods 12 is illustrated as being organized in a matrix assembly having a square cross section. Spacers 13 are typically provided for correctly spacing each fuel rod from adjacent fuel rods in a well known manner. Upper tie plate 14 is also well known in the art and is usually formed by a housing having four side walls 15. Leaf springs 17 are arranged along the upper edges 16 of the side walls 15 to provide proper tensioning force of the fuel assembly with core internals. Corner clamps 18a and 18b, which are each typically formed by an angle assembly, are used for holding down one end of the leaf springs 17. Each corner clamp has at least two hold down bolts 20. Each hold down bolt has a bolt head 21 (see FIG. 5) with an upper bolt head portion 21a and a lower bolt head portion 21b. The bolt has a shank 22 and a threaded relief portion 23. Slots 24 (see FIGS. 2 and 5) are provided in the upper bolt head portion 21a of head 21 in order to accommodate an anti-rotation bar 25 once the bolt has been set in place. Anti-rotation bar 25 is welded on both ends to a corner clamp 18a or 18b. Bolts 20a, 20b, 20c and 20d will extend through one of the corner clamps 18a or 18b into a receiving bore in the upper edges 16 of side walls 15 of the upper tie plate 14. Mating threads are provided in each receiving bore.

In the arrangement illustrated in FIG. 1, corner clamps 18a and 18b are provided at opposite corners 26 and 27 respectively of upper tie plate 14. Guide pin holes 30 and 31 are provided at corners 28 and 29 respectively of the upper tie plate 14. Pin holes 30 and 31 afford a means for inserting guide pins for proper aligning of fuel assembly mating parts.

Referring now to FIGS. 3A, 3B, 3C, and 4, inspection fixture 35 includes a support plate 36 which has a top surface 37 and a bottom surface 38. A corner guide pin assembly 40 is located at each of the opposite corners C1 and C3 of plate 36. Each guide pin assembly 40 includes a straight section 41, which depends from bottom surface 38 of plate 36, a tapered section 69 depending from straight section 41 and a bearing shoulder 42 at the transition between straight section 41 and tapered section 69. Straight section 41 has a dimension D defining the distance from bottom surface 38 to bearing shoulder 42. The guide pin assemblies 40 are arranged to align with guide pin holes 30 and 31 of the upper tie plate 14 in order to align fixture 35 with respect to the upper tie plate 14. In particular, tapered sections 69 of each guide pin assembly 40 is used for mating with one of the guide pin holes 30 or 31 in order to insure that fixture 35 is properly located with respect to upper tie plate 14. While pin holes 30 and 31 may be used for aligning upper tie plate 14 with other parts of the reactor, they are also available for use to align fixture 35, as described above.

When positioning fixture 35 with respect to upper tie plate 14, as tapered sections 69 of each guide pin assembly 40 are inserted into pin holes 30 or 31, bearing shoulder 42 will come to rest on the flat surface of upper tie plate 14 surrounding each pin hole so that dimension D predetermines the distance that plate 36 of fixture 35 will be spaced from upper tie plate 14.

An adjustable bearing pin 43 is located at each of corners C2 and C4 of plate 36. Each bearing pin 43 has a nut and bolt arrangement 43A and a bearing plate 43B at the distal end of the bolt. Nut and bolt arrangement 43A can be adjusted in order to adjust the distance d from bottom surface 38 of plate 36 to the bearing surface 43C of bearing plate 43B. When fixture 35 is positioned proximate to upper tie plate 14 with tapered sections 69 located in pin holes 30 and 31, bearing surface 43C will come to bear on corner clamps 18a and 18b. Adjustment of distance d can be made by nut and bolt arrangement 43A to insure that plate 36 is positioned paralleled to upper tie plate 14.

Plate 36 supports corner adjustable probe clamps 45a and 45b at corner C4 of the plate 36 and adjustable probe clamps 46a and 46b at the opposite corner C2 of plate 36. Each probe clamp is adapted to support a probe through an opening 47 in the support plate 26. Accordingly, there are four such openings 47. In the embodiment illustrated there are four probes 71, 72, 73 and 74 each of which extends through an opening 47. Probes 71 and 72 are supported in adjustable probe clamps 45a and 45b respectively, while probes 73 and 74 are supported in probe clamps 46a and 46b respectively. Each of the four probes support an ultrasonic transducer 75. Each probe clamp 45a, 45b, 46a and 46b is adjustable so as to properly position the transducers.

Plate 36 is provided with a plurality of openings 76 to allow passage of water so as to minimize water pressure on the plate 36 when fixture 35 is lowered into the fuel assembly below water. Sheaths 82 depend from fixture support plate 36 in order to provide protection against damage to the probes carrying ultrasonic transducers 75.

A riser 77 is secured to fixture support plate 36. Support rod 78 is secured to riser 77. Support rod 78 has a spring loaded U-joint 79 with spring 80 surrounding the support rod to provide proper tensioning on the spring loaded U-joint 79. Spring 80 is positioned between pins 81 and 83. The upper end of the support rod 78 is connected to pole sections for proper manipulation of the fixture 35 under the surface of the water.

Figure 5:
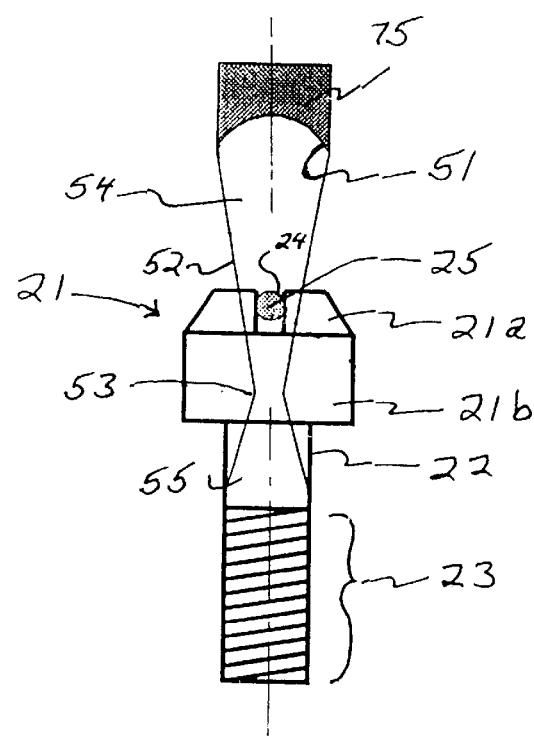
FIG. 5 is a side elevation view of a hold down bolt together with a schematic representation of an ultrasonic transducer head utilized in the present invention and a sound scanning field emanating from the transducer head.

When inspection fixture 35 is brought into proximity with tie plate 14 and is properly aligned therewith by using tapered sections 69 to mate with appropriate guide pin holes on the upper tie plate 14, transducers 75 of each probe 71, 72, 73 and 74 will have its longitudinal axis aligned with the longitudinal axis of the hold down bolts 20a, 20b, 20c and 20d respectively (see FIG. 5). When bearing surfaces 43C of bearing pin 43 on fixture 35 are brought into contact with corner clamps 18a and 18b respectively of the upper tie plate, and bearing shoulder 42 contacts the surface of the upper tie plate surrounding the pin holes 30 and 31, dimension D of straight sections 41 of the guide pin assemblies 40 will provide proper spacing of the transducer heads 75 from the top of the bolt heads 21 of each bolt 20a, 20b, 20c and 20d respectively.

When the inspection fixture 35 is properly positioned and the ultrasonic transducers are activated, each transducer head will produce a sound field. FIG. 5 illustrates the positioning of transducer head 75 having a spherically shaped concave lense 51 to produce a sound field 52 which is focused down to a focal point 53. The sound field 52 has an hour glass shape with an upper conical field 54 and a lower conical field 55. The focal point 53 forms the waist of the hour glass.

By determining the appropriate dimension D of straight section 41 of the guide pin assembly 40, focal point 53 of the sound field will be located near the bottom of lower portion 21b of the bolt head 21. By thus positioning the top of the bolt with slots 24 in the upper field 54, scattering of the sound from the transducers will be minimized. Further, by predetermining the position of the focal point just above the bottom of the bolt head portion 21b will permit expansion of the sound field 55 to be contained by the bolt shank 22 above the thread relief field 23. Containing the sound field in this area will greatly increase inspection sensitivity.

Figure 6:
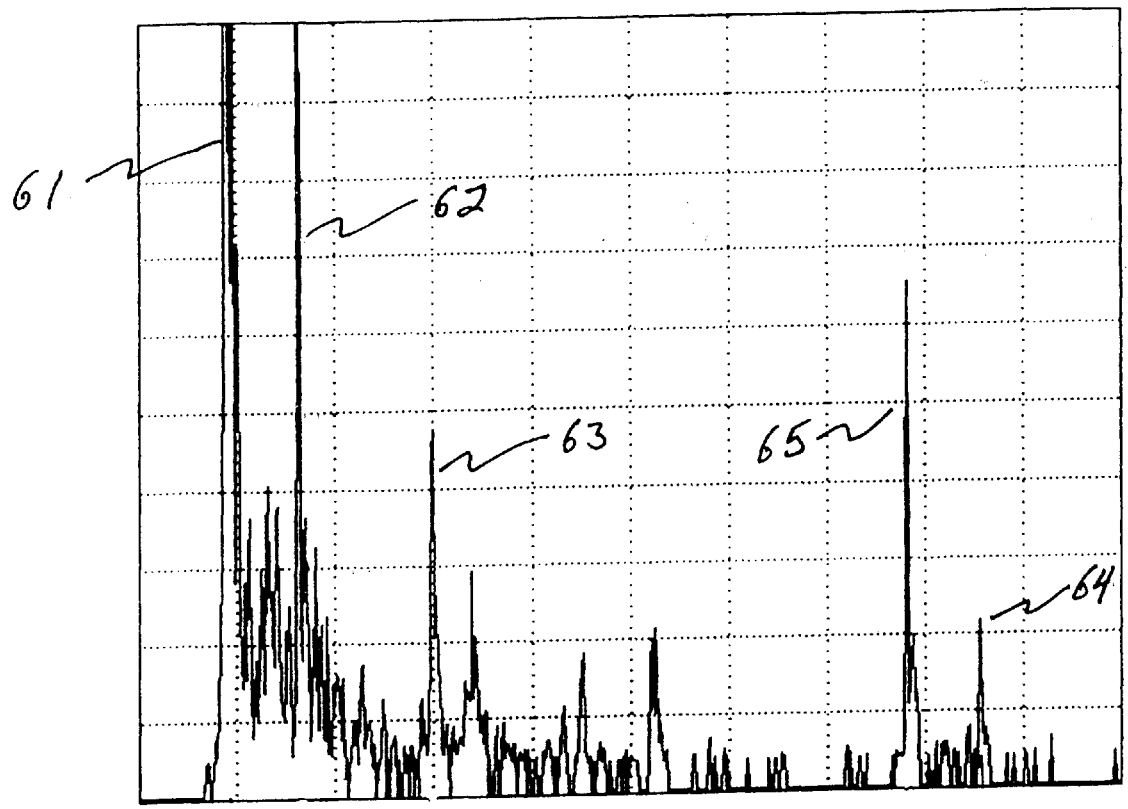
FIG. 6 is a representation of an ultrasonic signal identifying a flaw.

Each of the transducers 75 are connected, as indicated by connection lines 59, to a multi-channel ultrasound flaw detector 60 of well known and commercially available type. Ultrasonic flaw detector 60 is capable of reading the sound scan over a predetermined range. FIG. 6 illustrates a typical scan over a prescribed period of inspection time. The scan shown in FIG. 6 illustrates a spike 61 indicating the top of the bolt head and a spike 62 indicating the bottom of the anti-rotation slot 24. Another spike 63 illustrates the bottom of the bolt head. Spike 64 indicates a thread in the thread field 23, while spike 65 illustrates a crack or defect in the thread relief. It has been found that defects consisting of a crack or cut as small as 0.100 inches in the thread relief region is easily detected by the apparatus and method of this invention regardless of the rotational position of the bolt or the rotational position of any possible defect under the bolt head features.

Thus it will be appreciated that the present invention provides a rapid indication of possible flaws or cracks in the bolt shank without having to remove the bolt for visible or other types of inspection. The use of the inspection fixture having specially adapted spherical transducer heads enables rapid, inexpensive, insitu inspection of the bolts.

The invention has been described and illustrated in connection with a certain preferred embodiment which illustrates the principles of the invention. However, it should be understood that various modifications and changes may readily occur to those skilled in the art, and it is not intended to limit the invention to the construction and operation of the embodiment shown and described herein. Accordingly, additional modifications and equivalents may be considered as falling within the scope of the invention as defined by the claims herein below.

What is claimed is:

1. An apparatus for ultrasonically inspecting spring hold down bolts of an upper tie plate of a fuel rod assembly in a nuclear reactor comprising:
    an inspection fixture adapted to be aligned with an upper tie plate of a nuclear reactor fuel rod assembly and adapted to be placed into an inspection position located in proximity with said upper tie plate for effective ultrasonic inspection of said hold down bolts of said upper tie plate;
    at least one ultrasonic transducer carried by said fixture and positioned thereon so that each transducer is position for effective ultrasonic scanning of a hold down bolt of said upper tie plate in order to detect a predetermined minimum sized flaw in said hold down bolt when said fixture is placed in said inspection position and said transducer is activated;
    guide pin assemblies carried by the fixture configured to align the fixture with the upper tie plate; and
    a multi-channel ultrasonic flaw detector connected to said at least one ultrasonic transducer for indicating a possible flaw in each of said hold down bolts when said fixture is placed in said inspection position.

2. The apparatus for inspecting spring hold down bolts according to claim 1 wherein said ultrasonic transducer is a spherical transducer for focusing its sound field at a predetermined location.

3. The apparatus for inspecting spring hold down bolts according to claim 2 wherein said sound field is focused to a point just above the bottom of the head of said hold down bolt.

4. The apparatus for inspecting spring hold down bolts according to claim 3 wherein said sound field occurs along a double cone forming an hour glass configuration, and wherein the waist of said hour glass coincides with said focal point.

5. The apparatus for inspecting hold down bolts according to claim 1 wherein an ultrasonic transducer is provided for each spring hold down bolt on said upper tie plate.

6. The apparatus for inspecting spring hold down bolts according to claim 5 wherein said ultrasonic transducers are arranged in pairs.

7. The apparatus for inspecting spring hold down bolts according to claim 1 wherein said fixture comprises a fixture support plate having means for supporting said ultrasonic transducer.

8. The apparatus for inspecting spring hold down bolts according to claim 7 wherein said fixture support plate is provided with a plurality of holes to accommodate the passage of water therethrough.

9. The apparatus for inspecting hold down bolts according to claim 7 further comprising adjustable probe clamps mounted on said fixture support plate for supporting therein detector probes.

10. The apparatus for inspecting spring hold down bolts according to claim 9 wherein said probes carry said ultrasonic transducer.

11. The apparatus for inspecting spring hold down bolts according to claim 1 wherein said guide pin assemblies comprise a straight section, a tapered section connected to said straight section and a bearing shoulder at the connection of said straight section with said tapered section.

12. An apparatus for ultrasonically inspecting spring hold down bolts of an upper tie plate of a fuel rod assembly in a nuclear reactor comprising:

an inspection fixture adapted to be aligned with an upper tie plate of a nuclear reactor fuel rod assembly and adapted to be placed into an inspection position located in proximity with said upper tie plate for effective ultrasonic inspection of said hold down bolts of said upper tie plate, wherein said fixture comprises a fixture support plate having means for supporting said ultrasonic transducer;

at least one ultrasonic transducer carried by said fixture and positioned thereon so that each transducer is positioned for effective ultrasonic scanning of a hold down bolt of said upper tie plate in order to detect a predetermined minimum sized flaw in said hold down bolt when said fixture is placed in said inspection position and said transducer is activated;

a multi-channel ultrasonic flaw detector connected to said at least one ultrasonic transducer for indicating a possible flaw in each of said hold down bolts when said fixture is placed in said inspection position;

adjustable probe clamps mounted on said fixture support plate for supporting therein detector probes which carry said ultrasonic transducer;

guide pin assemblies carried by said fixture for aligning said fixture with said upper tie plate, wherein said guide pin assemblies comprise a straight section, a tapered section connected to said straight section and a bearing shoulder at the connection of said straight section with said tapered section; wherein said bearing shoulder is spaced from said fixture support by a distance which determines the distance that said transducer is spaced from the top of said bolt when said bearing shoulder is in contact with a surface of said upper tie plate.

13. The apparatus for inspecting hold down bolts according to claim 12 wherein said tapered section is adapted to mate with pin holes in said upper tie plate for positioning said fixture in alignment with said upper tie plate.

14. The apparatus for inspecting hold down bolts according to claim 13 further comprising at least one adjustable bearing pin carried by said fixture plate for insuring that said fixture plate is positioned parallel to said upper tie plate when said bearing shoulder is in contact with said surface of said upper tie plate.

15. The apparatus for inspecting spring hold down bolts according to claim 14 further comprising a riser connected to said fixture plate and a support rod connected to said riser in order to manipulate said fixture.

16. The apparatus for inspecting spring hold down bolts according to claim 12, wherein the ultrasonic transducer is a spherical transducer for focusing a sound field at a predetermined location.

17. The apparatus for inspecting spring hold down bolts according to claim 16, wherein the sound field is focused to a point just above the bottom of the head of said hold down bolt.

18. The apparatus for inspecting spring hold down bolts according to claim 17, wherein said sound field occurs along a double cone forming an hour glass configuration, and wherein the waist of the hour glass coincides with the focal point.

19. The apparatus for inspecting hold down bolts according to claim 12, wherein an ultrasonic transducer is provided for each spring hold down bolt on the upper tie plate.

20. The apparatus for inspecting hold down bolts according to claim 19, wherein the ultrasonic transducer is a pair of transducers.

21. The apparatus for inspecting hold down bolts according to claim 12, wherein the fixture support plate is configured with a plurality of holes to accommodate passage of water therethrough.

22. The apparatus for inspecting hold down bolts according to claim 12, further comprising:

a riser connected to the fixture plate and a support rod connected to the riser in order to manipulate the fixture.

* * * * *